United States Patent [19]

Darsow et al.

[11] Patent Number: 5,741,929
[45] Date of Patent: Apr. 21, 1998

[54] PROCESS FOR PREPARING A MIXTURE OF AMINO-METHYL-CYCLOHEXANES AND DIAMINO-METHYL-CYCLOHEXANES

[75] Inventors: Gerhard Darsow, Krefeld; Gerd-Michael Petruck, Erkrath, both of Germany

[73] Assignee: Bayer Aktiengesellschaft, Leverkusen, Germany

[21] Appl. No.: 814,184

[22] Filed: Mar. 10, 1997

[30] Foreign Application Priority Data

Mar. 18, 1996 [DE] Germany ............... 196 10 545.5

[51] Int. Cl.$^6$ ............................................. C07C 209/72
[52] U.S. Cl. ................................. 564/450; 564/451
[58] Field of Search ........................... 564/450, 451

[56] References Cited

U.S. PATENT DOCUMENTS

| | | | |
|---|---|---|---|
| 3,424,792 | 1/1969 | Cross | 564/461 |
| 3,445,516 | 5/1969 | Cross | 564/451 |
| 3,520,928 | 7/1970 | Greco | 564/450 |
| 4,161,492 | 7/1979 | Weissel | 564/305 |
| 4,186,145 | 1/1980 | Weissel | 564/451 |
| 4,943,549 | 7/1990 | Immel et al. | 502/304 |

FOREIGN PATENT DOCUMENTS

| | | |
|---|---|---|
| 0091028 | 10/1983 | European Pat. Off. . |
| 0351661 | 1/1990 | European Pat. Off. . |
| 0668101 | 8/1995 | European Pat. Off. . |
| 1618638 | 2/1971 | Germany . |
| 2024858 | 7/1971 | Germany . |
| 2132547 | 1/1973 | Germany . |
| 2502893 | 7/1976 | Germany . |
| 2745172 | 4/1979 | Germany . |
| 1298506 | 12/1972 | United Kingdom . |

*Primary Examiner*—Richard L. Raymond
*Attorney, Agent, or Firm*—Sprung Kramer Schaefer & Briscoe

[57] ABSTRACT

For the continuous preparation of a mixture of amino-methyl-cyclohexanes and diamino-methyl-cyclohexanes by catalytic hydrogenation of diamino-toluenes with hydrogen at temperatures of from 150° to 260° C. and an $H_2$ pressure of from 20 to 500 bar, use is made of a fixed-bed catalyst comprising ruthenium on an $Al_2O_3$ support treated with compounds of rare earth metals, of manganese and alkali metal hydroxides or alkaline earth metal hydroxides.

20 Claims, No Drawings

5,741,929

1

PROCESS FOR PREPARING A MIXTURE OF AMINO-METHYL-CYCLOHEXANES AND DIAMINO-METHYL-CYCLOHEXANES

BACKGROUND OF THE INVENTION

1. Field of the Invention

The invention relates to a continuous process for preparing a mixture of amino-methyl-cyclohexanes and diamino-methyl-cyclohexanes in variable amounts by catalytic hydrogenation of diamino-toluenes with hydrogen at elevated temperature using a fixed-bed ruthenium catalyst on an $Al_2O_3$ support treated with compounds of rare earth metals, of manganese and alkali metal hydroxides or alkaline earth metal hydroxides.

Amino-methyl-cyclohexanes are used for preparing aging inhibitors for rubbers and plastics, as corrosion inhibitors and as precursors for textile auxiliaries and crop protection agents.

Diamino-methyl-cyclohexanes are used for producing powder coating hardeners, epoxy hardeners, light-fast surface coating resins and aqueous surface coating resin dispersions.

2. Description of the Related Art

It is known that diamino-methyl-cyclohexanes can be prepared by pressure hydrogenation of diamino-toluenes. In this hydrogenation carried out batchwise, catalysts used are nickel alloys with molybdenum, ruthenium, tantalum, titanium (EP 091 028) or cobalt oxide (DE 16 18 638/DE 2 024 858/JP 71-64-898).

Other batchwise processes employ noble metals on supports, for example rhodium on $Al_2O_3$ (JP-83-89 242), platinum and palladium on carbon (U.S. Pat. No. 3,520,928) or ruthenium on $Al_2O_3$, $SiO_2$ or carbon (DE 2 132 547/JP 74-141 907) or ruthenium, chromium and manganese on $Al_2O_3$ (German Offenlegungsschrift 2 502 893/German Offenlegungsschrift 2 745 172), wherein the experimental examples describe exclusively batchwise processes and the reaction products mentioned are exclusively diamino-methyl-cyclohexanes.

Amino-methyl-cyclohexanes are obviously not formed at all in these reactions. In order to obtain amino-methyl-cyclohexanes in relatively large mounts, they are prepared by separate processes. Thus, for example, 1-amino-4-methyl-cyclohexane is prepared by hydrogenation of p-toluidine over a palladium (platinum)/carbon catalyst (U.S. Pat. No. 3,520,928).

A problem which is common to the processes for the ring-hydrogenation of methyl-substituted aromatic amines is the sometimes considerable formation of methyl- and amino-substituted dicyclohexyl-amines as unusable by-products. It is therefore desirable to develop a continuous fixed-bed process which can also be used on an industrial scale, by means of which both monoamino-methyl-cyclohexanes and diamino-methyl-cyclohexanes can be prepared in a desired ratio, in which losses resulting from the undesired formation of methyl- and amino-substituted dicyclohexyl-amines are avoided and in which, furthermore, the longest possible life of the catalyst used is sought.

SUMMARY OF THE INVENTION

It has now surprisingly been found that the abovementioned requirements are met by the use of a fixed-bed catalyst comprising as active constituents ruthenium, compounds of rare earth metals, of manganese and of alkali metals and/or alkaline earth metals, preferably of alkaline earth metals, which are applied to an $Al_2O_3$ support.

2

The invention accordingly provides a continuous process for preparing a mixture of amino-methyl-cyclohexanes and diamino-methyl-cyclohexanes of the formulae

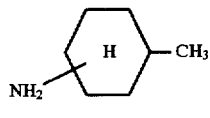

and

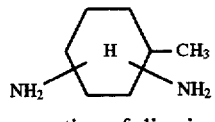

by catalytic hydrogenation of diamino-toluenes of the formula

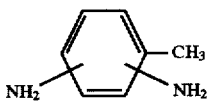

with hydrogen at reaction temperatures of from 150° to 260° C. and an $H_2$ pressure of from 20 to 500 bar, wherein the catalyst used comprises ruthenium together with compounds of rare earth metals, of manganese and alkali metal hydroxides and/or alkaline earth metal hydroxides on an $Al_2O_3$ support.

DETAILED DESCRIPTION OF THE INVENTION

Suitable supports are aluminum oxides quite generally. Preference is given to using α- or γ-$Al_2O_3$ as support, particularly preferably γ-$Al_2O_3$.

The support is doped with one or more compounds of rare earth metals and of manganese. The content of rare earth metals and manganese, calculated as metal, is together from 0.1 to 8% by weight, preferably from 0.3 to 5% by weight, based on the total weight of the catalyst. The weight ratio of rare earth metals to manganese is from 5:1 to 1:5, preferably from 2:1 to 1:2. For the purposes of the present invention, rare earth metals are the elements of transition group III of the Periodic Table (Mendeleev), for example scandium, yttrium, lanthanum and the lanthanides. Preference is given to using yttrium, lanthanum, cerium, praseodymium, neodymium and dysprosium, particularly preferably cerium and lanthanum and very particularly preferably cerium. The rare earth metals frequently occur in association with one another. The particularly preferred cerium can be associated, for example, with lanthanum, praseodymium, neodymium, dysprosium or with yttrium or with a plurality of these. A person skilled in the art is familiar with such an association for all rare earth metals mentioned.

The noble metal ruthenium, which acts as further active constituent, is present in a total amount of from 0005 to 5% by weight, preferably from 0.05 to 4% by weight, particularly preferably from 0.1 to 3% by weight, based on the total weight of the catalyst.

The catalysts to be used according to the invention can be produced by applying compounds of the rare earth metals and of manganese to the aluminum oxide support in the form of extrudates, pellets or spheres having diameters of from about 2 to 10 mm. The support doped in this way is, after drying, heated to from 200° to 450° C. and subsequently impregnated or sprayed with a solution of a ruthenium salt, after which it is dried again.

The application of compounds of the rare earth metals and of manganese to the catalyst support can be carried out, for example, by simple impregnation or spraying with aqueous solutions of suitable salts of the rare earth metals and of manganese. The application of compounds of the rare earth metals and of manganese can, however, also be carried out by coprecipitation of a rare earth metal/manganese hydroxide mixture onto the support from rare earth metal and manganese salts using alkali metal hydroxide solution or ammonia and, if desired, subsequent washing out of the soluble components using water. Suitable rare earth metal and manganese salts are, in particular, the sulfates, chlorides, acetates and/or nitrates of the elements mentioned. After application of the rare earth metal and manganese salts and, if desired after the precipitation described and the subsequent washing out of water-soluble compounds, the support thus treated is first dried before it is heated to the specified higher temperature, from about 200° to 450° C., preferably from 250° to 430° C. This heating is carried out over a period of from 1 to 120 hours. During this time, the temperature can be increased within the range indicated from lower to higher values.

After the heat treatment described, the catalyst support doped in this way is impregnated with a ruthenium-containing solution. This can be carried out by impregnating or spraying the support with ruthenium, for example in the form of aqueous solutions of the chloride, nitrate, acetate or another suitable salt, followed by drying. If desired, the ruthenium salts can also be dissolved in organic solvents such as methanol, acetonitrile or dioxane and applied in this form. However, it is also possible for the support impregnated with ruthenium salts to be treated before drying with an aqueous solution of the abovementioned basic compounds, thus precipitating the ruthenium as oxide or hydroxide. This variant of the application of ruthenium is also followed by drying. However, it is also possible for the catalyst support treated with compounds of the rare earth metals and of manganese to be first impregnated with the solution of one of the basic compounds mentioned, subsequently dried and solutions of ruthenium salts to be applied to the catalyst support which has been pretreated in this way and made basic, with the precipitation of the ruthenium in the form of its oxide or hydroxide also occurring at the moment of impregnation.

The catalyst to be used additionally contains from 1 to 6% by weight, preferably from 2 to 5% by weight, based on the total weight of the catalyst, of one or more alkali metal hydroxides or from 0.5 to 10% by weight, preferably from 1 to 7% by weight, likewise based on the total weight of the catalyst, of one or more alkaline earth metal hydroxides. Alkali metal hydroxides are lithium hydroxide, sodium hydroxide, potassium hydroxide, rubidium hydroxide, cesium hydroxide, preferably lithium hydroxide, sodium hydroxide, potassium hydroxide, particularly preferably sodium hydroxide or potassium hydroxide. Alkaline earth metal hydroxides are beryllium hydroxide, magnesium hydroxide, calcium hydroxide, strontium hydroxide, barium hydroxide or mixtures of the above compounds, preferably calcium hydroxide, strontium hydroxide, barium hydroxide, particularly preferably strontium hydroxide and/or barium hydroxide.

The application of the alkali metal hydroxides or alkaline earth metal hydroxides is followed by drying, in general at from 100° to 140° C. under reduced to atmospheric pressure (from 1 to 1000 mbar, preferably from 10 to 500 mbar, for example in a water pump vacuum).

Impregnation with the ruthenium and the alkali metal hydroxides or alkaline earth metal hydroxides is carried out separately. Here, the support can first be impregnated with the ruthenium in the above described manner and, after drying, be impregnated again with alkali metal hydroxides or alkaline earth metal hydroxides. During this treatment, the ruthenium is precipitated in the form of its oxide or hydroxide. The alkali metal hydroxides or the alkaline earth metal hydroxides can be applied separately or together. However, it is also possible for the support to first be impregnated with an alkali metal hydroxide solution or an alkaline earth metal hydroxide solution, subsequently dried and salts of ruthenium to be applied to the catalyst support which has been pretreated in this way and made basic, with the precipitation of the ruthenium in the form of the oxide or hydroxide also appearing at the moment of impregnation. Instead of impregnation with the salt solutions mentioned, they can also be sprayed on. The equipment required for this purpose and the setting of the desired amounts applied by selection of the amount and concentration of the solutions of the specified materials are known in principle to those skilled in the art.

After the last drying phase, a supported catalyst prepared in the above way is in principle ready for use according to the invention. However, it is preferably activated prior to use, particularly preferably after installation in the hydrogenation reactor, by treatment with hydrogen at a temperature of from 150° to 400° C.

Suitable starting materials for the hydrogenation according to the process of the invention are, for example: 2,4-diamino-toluene, 2,5-diamino-toluene, 2,6-diaminotoluene or mixtures of these compounds.

The process of the invention using the catalysts described forms mixtures of amino-methyl-cyclohexanes and diamino-methyl-cyclohexanes. Surprisingly, the ratio of the amines can be changed as a function of the hydrogenation temperature, viz. more amino-methyl-cyclohexanes are formed with increasing temperature and the opposite effect is obtained with decreasing temperature.

The process of the invention is carried out, for example, in the gas phase or a trickling phase using the catalyst arranged in a fixed bed. It is carried out using an excess of hydrogen; the amount of $H_2$ is from 10 to 120 times the amount, preferably from 10 to 80 times the amount, which is required for the hydrogenation of one benzene ring.

The process is carried out at from 150° to 260° C., preferably at from 160° to 250° C., and at a pressure of at least 20 bar, preferably at least 100 bar, particularly preferably at least 200 bar. The upper limit of the pressure employed is determined by both technical and economic considerations and is 500 bar, preferably from 200 to 400 bar.

The weight hourly space velocity over the catalyst is from 0.05 to 2 kg, preferably from 0.1 to 1 kg, particularly preferably from 0.15 to 0.6 kg, of diamino-toluenes per liter of catalyst per hour. A slight change in the proportion of amino-methyl-cyclohexanes achieved resulting from changed activity of the catalyst during the course of particularly long reaction-periods can be compensated by a slight adjustment of the reaction temperature or of the other parameters. These circumstances can be monitored by analysis of the reaction mixture.

The catalyst to be used according to the invention can be installed in various apparatuses known in principle for such purposes to those skilled in the art. The process of the invention is advantageously carried out in tube reactors having one or more tubes. The reaction tubes can have lengths of, for example, from 2 to 20 m and internal diameters of from 20 to 800 mm. The catalysts have, for example, dimensions of from 2 to 10 mm and are, for example, in the form of extrudates, pellets or spheres.

The process of the invention can be carried out with or without solvents. Suitable solvents which are inert under the reaction conditions are, for example, methanol, ethanol, isopropanol.

The catalysts used according to the invention have very long operating lives; up to now from 12,000 to 15,000 hours have been observed, after which the experiments were stopped without any noticeable decrease in the activity.

The reaction mixtures obtained after the hydrogenation contain virtually no methyl-substituted amino-di-N-cyclohexanes, so that particularly high contents of amino-methyl-cyclohexanes and diamino-methyl-cyclohexanes can be achieved.

The hydrogenation mixtures can be worked up by simple distillation. For such a work-up, it can be advantageous to react the respective diamino-toluenes incompletely, because the ammonia liberated in the formation of the monoamino-methyl-cyclohexanes is very readily soluble in the diamino-toluenes and can thus be removed from the off-gas from the reaction. In the distillation of the reaction products, the dissolved ammonia is distilled off first, condensed and is thus available for further use; incompletely reacted diamino-toluenes can be returned to the reaction. The unconsumed path of the hydrogen used in excess can also be returned to the reaction; the major part of this unreacted hydrogen is advantageously recovered in a high-pressure separator so that the work of compression for the hydrogen does not have to be expanded again.

The amino-methyl-cyclohexanes and diamino-methyl-cyclohexanes prepared according to the invention are, after successful separation by distillation, obtained in a purity of at least 99.9% by weight. In this purity, the specified compounds are generally usable for all further processes.

The ability of the process of the invention to be varied is shown by a strong increase in the proportion of amino-methyl-cyclohexanes compared with the diamino-methyl-cyclohexanes with rising temperature and otherwise identical conditions. Thus, for example, the proportion of amino-methyl-cyclohexanes obtained in the temperature range from about 200° to 230° C. is from 2 to 10 times that in the temperature range from 170° to 185° C.

EXAMPLES

Example 1

2000 g of a commercial γ-$Al_2O_3$ having a specific surface area of 338 $m^2/g$ and a sphere diameter of from 2 to 4 mm were impregnated with a solution which had been prepared from 124 g of $Ce(NO_3)_3.6H_2O$, 182.8 g $Mn(NO_3)_2.4 H_2O$ and 750 g of water. The impregnated $Al_2O_3$ was dried for 18 hours at 120° C. and 200 mbar and subsequently heated for 8 hours at 420° C. 2000 g of the catalyst support thus treated were impregnated with 700 g of an aqueous $Ru(NO_3)_3$ solution containing 20 g of Ru. The moist catalyst was dried for 18 hours at 100° C. under a pressure of 200 mbar. 2000 g of the Ru-doped catalyst support were impregnated with an aqueous $Ba(OH)_2$ slurry containing 30 g of Ba. The moist catalyst was subsequently dried for 20 hours at 100° C. under a pressure of 200 mbar.

Example 2

2000 g of a commercial γ-$Al_2O_3$ having a specific surface area of 338 $m^2/g$ and a sphere diameter of from 2 to 4 mm were impregnated with a solution which had been prepared from 125 g of $La(NO_3)_3.6H_2O$, 178.5 g of $Mn(CH_3COO)_2.4 H_2O$ and 400 g of water. The $Al_2O_3$ thus impregnated was subsequently dried for 18 hours at 100° C. under a pressure of 200 mbar and then heated for 5 hours at 400° C. 500 g of the catalyst support thus treated were impregnated with 175 g of an aqueous $Ru(NO_3)_3$ solution containing 5 g of Ru. The moist catalyst was dried for 18 hours at 100° C. under a pressure of 200 mbar. 500 g of the Ru-doped catalyst support were impregnated with an aqueous $Sr(OH)_2$ slurry containing 5 g of Sr. The moist catalyst was subsequently dried for 20 hours at 100° C. under a pressure of 200 mbar.

Example 3

An upright, heat-insulated high-pressure tube of stainless steel having an internal diameter of 30 mm and a length of 1 m, which had previously been flushed oxygen-free using nitrogen, was charged with 400 ml of a spherical Ru/Ce/Mn/Ba-$Al_2O_3$ catalyst which had been prepared as described in Example 1 and contained 1% by weight of Ru, 2% by weight of Ce, 2% by weight of Mn and 1.5% by weight of Ba. To activate the catalyst, the catalyst spheres were first dried further for 6 hours in a stream of nitrogen (temperature: max. 200° C., flow: 1.5 standard $m^3$ of $N_2$/hd). The actual activation was carried out under a nitrogen pressure of 200 bar at a temperature between 150° and 350° C., with hydrogen being gradually mixed into the nitrogen. Over a period of 12 hours, the proportion of nitrogen was reduced more and more until finally only hydrogen flowed through the reactor.

After activation of the hydrogenation catalyst, the hydrogen pressure in the reactor system was increased to 300 bar. Subsequently, 100 g/h of 2,4-diamino-toluene together with 1000 standard l of hydrogen under a pressure of 300 bar were pumped through the high-pressure tube from the top downward. The 2,4-diamino-toluene was heated in an upstream, electrically heated heat exchanger to a temperature of 160° C. before entering the reactor. The reaction product leaving the reaction tube was cooled under 300 bar of hydrogen pressure to a temperature of <60° C. in a second heat exchanger (water cooler) and separated in a gas separator from excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (figures in % by area; the remainder to 100% is by-products):

| Running time (h) | Temperature (°C.) | 2- and 4-amino-methyl-cyclohexane (% by area) | 2,4-diamino-methyl-cyclohexane (% by area) | 2,4-diamino-toluene (% by area) |
| --- | --- | --- | --- | --- |
| 116 | 175 | 5.2 | 34.9 | 57.9 |
| 144 | 180 | 13.9 | 40.3 | 44.3 |
| 198 | 205 | 24.8 | 57.0 | 16.4 |
| 224 | 215 | 33.0 | 62.8 | 2.37 |
| 368 | 220 | 43.3 | 56.5 | 0.16 |

Example 4

An upright, heat-insulated high-pressure tube of stainless steel having an internal diameter of 30 mm and a length of 1 m, which had previously been flushed oxygen-free using nitrogen, was charged with 400 ml of a spherical Ru/La/

Mn/Sr-Al$_2$O$_3$ catalyst which had been prepared as described in Example 2 and contained 1% by weight of Ru, 2% by weight of La, 2% by weight of Mn and 1% by weight of Sr. To activate the catalyst, the catalyst spheres were first dried further for 8 hours in a stream of nitrogen (temperature: max. 200° C., flow: 1.5 standard m$^3$ of N$_2$/h). The actual activation was carried out under a nitrogen pressure of 200 bar at a temperature between 150° and 350° C., with hydrogen being gradually mixed into the nitrogen. Over a period of 12 hours, the proportion of nitrogen was reduced more and more until finally only hydrogen flowed through the reactor.

After activation of the hydrogenation catalyst, the hydrogen pressure in the reactor system was increased to 300 bar. Subsequently, 100 g/h of 2,6-diamino-toluene together with 1000 standard l of hydrogen under a pressure of 300 bar were pumped through the high-pressure tube from the top downward. The 2,6-diamino-toluene was heated in an upstream, electrically heated heat exchanger to a temperature of 160° C. before entering the reactor. The reaction product leaving the reaction tube was cooled under 300 bar of hydrogen pressure to a temperature of <60° C. in a second heat exchanger (water cooler) and separated in a gas separator from excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (figures in % by area; the remainder to 100% is by-products):

| Running time (h) | Temperature (°C.) | 2-amino-methyl-cyclohexane (% by area) | 2,6-diamino-methyl-cyclohexane (% by area) | 2,6-diamino-toluene (% by area) |
|---|---|---|---|---|
| 92  | 175 | 8.6  | 34.3 | 55.6 |
| 224 | 180 | 15.2 | 41.1 | 41.9 |
| 418 | 205 | 27.2 | 55.6 | 15.2 |
| 466 | 215 | 36.2 | 58.6 | 3.1  |
| 512 | 230 | 48.1 | 50.3 | 0.2  |

Example 5

An upright, heat-insulated high-pressure tube of stainless steel having an internal diameter of 30 mm and a length of 1 m, which had previously been flushed oxygen-free using nitrogen, was charged with 400 ml of a spherical Ru/Ce/Mn/Ba-Al$_2$O$_3$ catalyst which had been prepared as described in Example 1 and contained 1% by weight of Ru, 2% by weight of Ce, 2% by weight of Mn and 1.5% by weight of Ba. To activate the catalyst, the catalyst spheres were first dried further for 6 hours in a stream of nitrogen (temperature: max. 200° C., flow: 1.5 standard m$^3$ of N$_2$/h). The actual activation was carried out under a nitrogen pressure of 200 bar at a temperature between 150° and 350° C., with hydrogen being gradually mixed into the nitrogen. Over a period of 12 hours, the proportion of nitrogen was reduced more and more until finally only hydrogen flowed through the reactor.

After activation of the hydrogenation catalyst, the hydrogen pressure in the reactor system was increased to 300 bar. Subsequently, 80 g/h of a mixture of 80% by weight of 2,4-diamino-toluene and 20% by weight of 2,6-diamino-toluene together with 1000 standard l of hydrogen under a pressure of 300 bar were pumped through the high-pressure tube from the top downward. The diamino-toluene mixture was heated in an upstream, electrically heated heat exchanger to a temperature of 160° C. before entering the reactor. The reaction product leaving the reaction tube was cooled under 300 bar of hydrogen pressure to a temperature of <60° C. in a second heat exchanger (water cooler) and separated in a gas separator from excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (figures in % by area; the remainder to 100% is by-products):

| Running time (h) | Temperature (°C.) | 2- and 4-amino-methyl-cyclohexane (% by area) | 2,4- and 2,6-diamino-methyl-cyclohexane (% by area) | 2,4- and 2,6-diamino-toluene (% by area) |
|---|---|---|---|---|
| 566  | 210 | 23.9 | 63.5 | 12.9 |
| 1938 | 155 | 3.1  | 19.4 | 76.1 |
| 2008 | 160 | 5.2  | 27.8 | 65.3 |
| 2056 | 165 | 8.9  | 39.1 | 49.6 |
| 2154 | 185 | 10.1 | 44.9 | 44.4 |
| 2176 | 195 | 16.1 | 53.1 | 29.8 |
| 2224 | 200 | 16.4 | 61.0 | 22.1 |
| 2272 | 210 | 22.8 | 63.7 | 13.2 |
| 2424 | 220 | 33.0 | 65.1 | 1.1  |

What is claimed is:

1. A continuous process for preparing a mixture of an amino-methyl-cyclohexane and a diamino-methyl-cyclohexane of the formulae

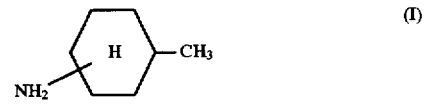

and

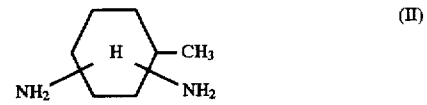

by catalytic hydrogenation of a diamino-toluene of the formula

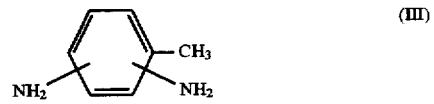

with hydrogen at reaction temperatures of from 150° to 260° C. and an H$_2$ pressure of from 20 to 500 bar, wherein the catalyst used comprises ruthenium on an Al$_2$O$_3$ support treated with compounds of rare earth metals, of manganese and alkali metal hydroxides and/or alkaline earth metal hydroxides.

2. The process of claim 1, wherein the support is α- or γ-Al$_2$O$_3$.

3. The process of claim 2, wherein the support is γ-Al$_2$O$_3$.

4. The process of claim 1, wherein the Al$_2$O$_3$ support comprises extrudates, pellets or spheres having dimensions of from about 2 to 10 mm.

5. The process of claim 1, wherein one or more compounds of rare earth metals and of manganese are applied to a γ-Al$_2$O$_3$ support and the content of rare earth metals and manganese, calculated as metal, is together from 0.1 to 8% by weight, based on the total weight of the catalyst, the weight ratio of rare earth metals to manganese is from 5:1 to 1:5 and the rare earth metals applied are the elements of transition group III of the Periodic Table (Mendeleev).

6. The process of claim 5, wherein the content of rate earth metals and manganese is together from 0.3 to 5% by weight.

7. The process of claim 5, wherein the weight ratio of rare earth metals to manganese is from 2:1 to 1:2.

8. The process of claim 5, wherein one or more compounds of rare earth metals are of the group of scandium, yttrium, lanthanum and the lanthanides, preferably yttrium, lanthanum, cerium, praseodymium, neodymium and dysprosium.

9. The process of claim 8, wherein the rare earth metals are of the group of cerium and lanthanum.

10. The process of claim 1, wherein a $\gamma$-$Al_2O_3$ support has ruthenium applied to it in a total amount of from 0.05 to 5% by weight based on the total weight of the catalyst.

11. The process of claim 1, wherein a $\gamma$-$Al_2O_3$ support has one or more alkali metal hydroxides applied to it in a total amount of from 1 to 6% by weight, based on the total weight, or one or more alkaline earth metal hydroxides in a total amount of from 0.5 to 10% by weight, likewise based on the total weight, where the alkali metal hydroxide(s) is/are lithium hydroxide, sodium hydroxide, potassium hydroxide, rubidium hydroxide, cesium hydroxide and the alkaline earth metal hydroxide(s) is/are beryllium hydroxide, magnesium hydroxide, calcium hydroxide, strontium hydroxide, barium hydroxide.

12. The process of claim 11, wherein one or more alkali metal hydroxides are applied in a total amount of from 2 to 5% by weight.

13. The process of claim 11, wherein one or more alkaline earth metal hydroxides are applied in a total amount of from 1 to 7% by weight.

14. The process of claim 11, wherein one or more alkali metal hydroxides are of the group of lithium hydroxide, sodium hydroxide and potassium hydroxide.

15. The process of claim 11, wherein one or more alkaline earth metal hydroxide are of the group of calcium hydroxide, strontium hydroxide and barium hydroxide.

16. The process of claim 1, carried out at an $H_2$ pressure of from 100 to 400 bar.

17. The process of claim 1, carried out at a temperature of from 160° to 250° C.

18. The process of claim 1, carried out continuously in the gas phase or a trickling phase over fixed-bed catalysts at a weight hourly space velocity over the catalyst of from 0.05 to 2 kg of diamino-toluenes per liter of catalyst per hour.

19. The process of claim 1, wherein the catalyst is activated by treatment with hydrogen at a temperature of from 150° to 400° C. before use.

20. The process of claim 19, wherein the catalyst is activated after installation in the hydrogenation reactor.

\* \* \* \* \*